(12) United States Patent
DeLegge et al.

(10) Patent No.: US 8,647,324 B2
(45) Date of Patent: Feb. 11, 2014

(54) CATHETER ACCESS AND CONTROL DEVICE AND METHOD OF USING SAME

(76) Inventors: Rebecca Copenhaver DeLegge, Mount Pleasant, SC (US); Mark Henry DeLegge, Mount Pleasant, SC (US)

( * ) Notice: Subject to any disclaimer, the term of this patent is extended or adjusted under 35 U.S.C. 154(b) by 0 days.

(21) Appl. No.: 13/352,307

(22) Filed: Jan. 17, 2012

(65) Prior Publication Data

US 2012/0184896 A1     Jul. 19, 2012

Related U.S. Application Data

(60) Provisional application No. 61/433,773, filed on Jan. 18, 2011.

(51) Int. Cl.
    *A61M 25/01*      (2006.01)
(52) U.S. Cl.
    USPC ......................................................... 604/528
(58) Field of Classification Search
    USPC ......................................................... 604/528
    See application file for complete search history.

(56) References Cited

U.S. PATENT DOCUMENTS

| 7,377,906 | B2 * | 5/2008 | Selkee | 604/95.04 |
| 2009/0054921 | A1 * | 2/2009 | Yanuma | 606/191 |
| 2009/0112064 | A1 * | 4/2009 | Levey et al. | 600/114 |
| 2010/0004633 | A1 * | 1/2010 | Rothe et al. | 604/528 |

* cited by examiner

*Primary Examiner* — Laura Bouchelle
(74) *Attorney, Agent, or Firm* — B. Craig Killough; Barnwell Whaley Patterson Helms

(57) ABSTRACT

The present application discloses a handle configured to receive a catheter. The handle comprises a port that communicates with a lumen of the catheter and a mechanism is provided that moves the end of the catheter for positioning. The guide wire traverses a reservoir located in the handle. In particular, the handle comprises an enclosure with a conduit and a reservoir, where the conduit extends through the enclosure from the left side to the right side and the reservoir space has a curved or concave base. The bottom side and top side of the handle converge into a tapered point on the left side.

28 Claims, 13 Drawing Sheets

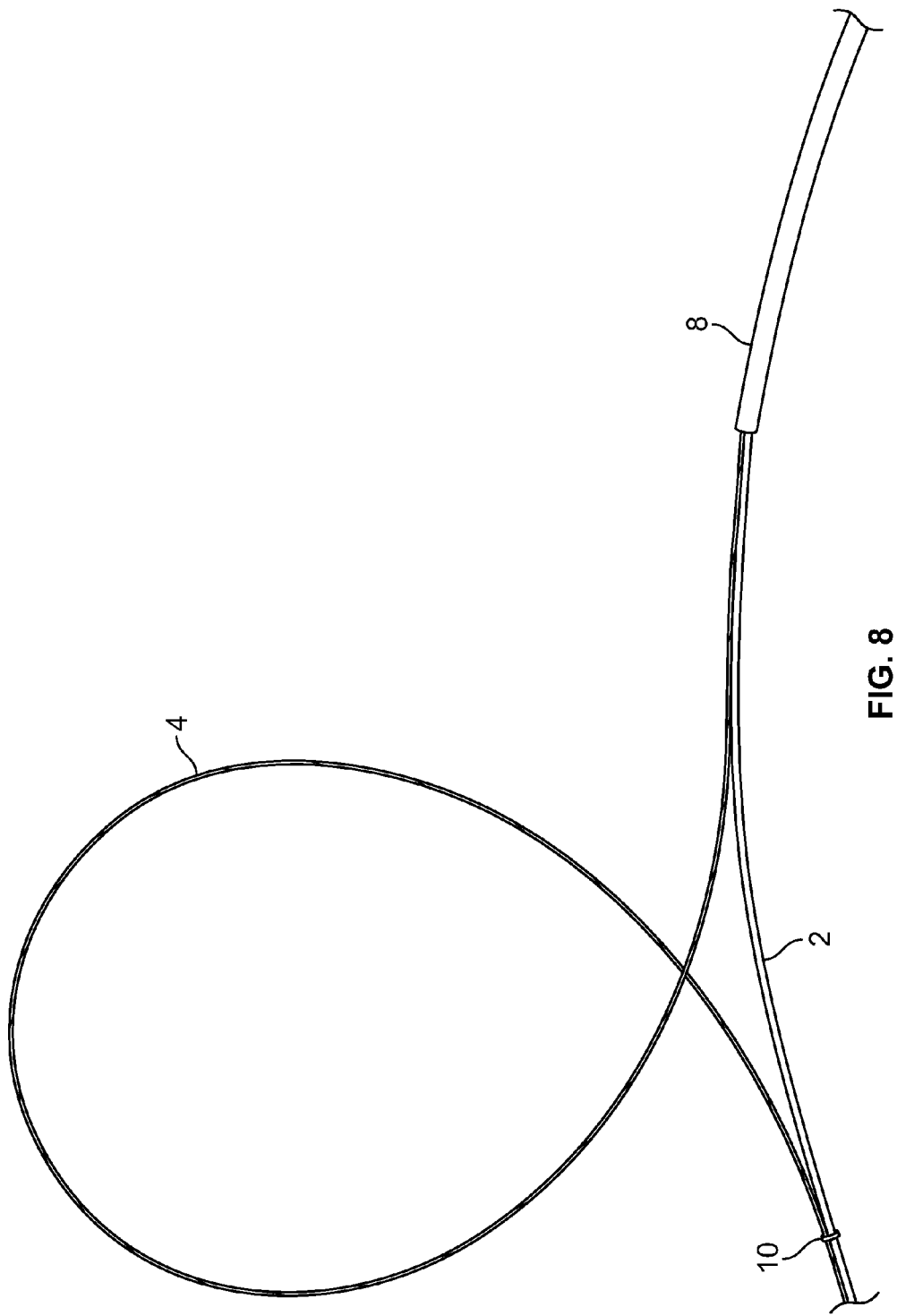

CATHETER ACCESS AND CONTROL DEVICE AND METHOD OF USING SAME

CROSS REFERENCE

The present application relies on U.S. Patent Provisional Application No. 61/433,773, filed on Jan. 18, 2011, and entitled "Catheter Access and Control Device and Method of Using Same". The aforementioned application is incorporated herein by reference in its entirety.

FIELD

The present application relates generally to devices and methods of positioning catheters, and specifically relates to a handle system that helps a user accurately and conveniently position a catheter.

BACKGROUND

Catheters in common use have one or more lumens that are insertible into humans or animals. Catheters are inserted into body cavities, ducts, or vessels to allow the passage of fluids or to distend a passageway. Catheters may be positioned in ducts or vessels using guide wires that are first inserted into the duct or vessel. One or more of the lumens may permit guide wires or similar strands that travel within, and relative to, the lumen.

In one application, a relatively long guide wire passes through the catheter and into the bile duct or pancreatic duct. The guide wire is positioned by an assistant at an end of a relatively long guide wire. A physician views the movement of the guide wire and directs the movement of the guide wire. Thus, the wire is positioned by the assistant under the guidance of the physician. In most cases, the physician is positioned between the assistant and the patient, as he holds the scope at approximately mid-catheter. For fine movements into the duct to cannulate, a physician may control the guide wire, but this process requires the physician and the assistant to swap positions, which may be inconvenient or may disturb the procedure. Access to the guide wire is at the end of the catheter where the assistant advances the wire into, and through, the lumen. After the wire is in place in the duct, the physician may continue to control the guide wire, or the physician may return control of wire management to the assistant, who holds the wire in place from the end of the catheter.

In another application, a relatively shorter guide wire passes through the catheter and into the bile duct or pancreatic duct. The guide wire is positioned by the physician from the time of insertion, during gross advancement of the guide wire and during fine positioning of the guide wire. A physician views the movement of the guide wire and personally directs the physical movement of the guide wire. In this "short wire" process, the physician typically controls the entire process.

In practice, neither the "short wire" nor the "long wire" process is completely satisfactory. The physician generally prefers that the assistant perform gross advancement of the guide wire, but the physician prefers to perform the finer moments of final positioning of the guide wire in the duct.

SUMMARY

In one embodiment, the present application discloses a handle configured to receive a catheter. A guide wire traverses the catheter and the handle. A lumen of the catheter has a split, void, partition, or any other type of separation. The separation in the lumen is constructed and arranged to allow the guide wire to be accessed through the lumen via the separation.

The handle comprises a port that communicates with a lumen of the catheter and a mechanism is provided that moves the end of the catheter for positioning. The guide wire traverses a reservoir located in the handle. The reservoir contains saline or other fluid material for lubrication of the guide wire. A control for the mechanism is provided on the handle and a control traverses a lumen in the catheter.

Gross positioning of the guide wire may be performed by an assistant positioned near an end of guide wire. The catheter allows accesses of the guide wire through the spilt and at an intermediate position. The physician may access the guide wire for fine positioning of the guide wire.

In another embodiment, the present application discloses a handle for use in medical procedures having a top side, bottom side, left side, and right side, comprising an enclosure having a first space and a second space, wherein said first space and said second space are not in fluid communication with each other, wherein said first space extends through the enclosure from the left side to the right side, and wherein the second space has a concave base. Optionally, the bottom side and top side converge into a tapered point on the left side. The first space is a conduit and extends through said tapered point on the left side.

Optionally, the bottom side comprises a plurality of peaks and valleys, wherein each valley is configured to receive a finger of a user. The bottom side has a surface that comprises at least one peak, wherein said at least one peak comprises a slot formed by protrusions extending outward from said surface. The second space is a reservoir and the right side comprises an input port in fluid communication with the reservoir and a fitting extending outward from said right side in fluid communication with the input port. The handle further comprises a back flow valve positioned within the conduit and proximate said input port. The handle further comprises a geared mechanism in physical communication with an interior region in said first space.

Optionally, the geared mechanism comprises a rotating structure and a linear structure, wherein said rotating structure is exposed through said top side, and wherein said rotating structure is configured such that, upon moving said rotating structure by a first distance, the linear structure is caused to move. The linear structure is in physical communication with the interior region of the first space, wherein, upon movement of said linear structure, a wire located within the first space will be moved a second distance. The first distance is half of said second distance.

Optionally, the handle further comprises a locking mechanism configured to lock a wire within said first conduit, wherein said locking mechanism comprises a member extending outward from the top side and a gasket in physical communication with the member and an interior of the first conduit. The handle further comprises a papillatome control, wherein said papillatome control extends outward from top side of the handle and is slidably connected to the handle. The papillatome control comprises a member that slides within a slot formed in the handle and is connected to a papillatome drive wire.

In another embodiment, the present application discloses a catheter for use in the handle embodiments disclosed herein, wherein the catheter comprises a sheath having an opening and a cylindrical member configured to slide from a first position to a second position over the sheath. The first position covers said opening and the second position does not cover said opening.

In another embodiment, the present application discloses a handle for use biliary work, gastrointestinal procedures, bronchoscopy procedures, stent placements, ERCP, pancreas cannulation, vascular vessel cannulation, peripheral vessel cannulation, urologic cannulation, minimally invasive spine, orthopedic procedures, and laparoscopic procedures, wherein said handle has a top region, middle region and bottom region and wherein said handle comprises an enclosure; a reservoir formed within said enclosure, wherein said reservoir is located substantially within the middle and bottom regions of the handle and wherein said reservoir has a substantially planar top surface and a curved bottom surface; an input port on a first side of the handle and proximate to the top surface of the reservoir; and a fitting extending outward from said right side in fluid communication with the input port.

Optionally, the handle comprises a bottom side and a top side and the bottom side and top side converge into a tapered point on a second side of the handle. The handle further comprises a conduit extending from a first side of the handle through said tapered point on the second side. The handle comprises a bottom side, wherein the bottom side has a surface that comprises at least one peak, and wherein said at least one peak comprises a slot formed by protrusions extending outward from said surface.

Optionally, the handle further comprises a wire moving mechanism wherein said wired moving mechanism comprises a first rotating structure and a second rotating structure, wherein said first rotating structure is exposed through a top surface of the handle, and wherein said first rotating structure is configured such that, upon moving said first rotating structure by a first distance, the second rotating structure is caused to move. The second rotating structure is in physical communication with an interior region of a conduit within the handle and wherein, upon movement of said second rotating structure, a wire located within the first space will be moved a second distance. The first distance is less than said second distance. The handle further comprises a locking mechanism configured to lock a wire within a conduit located in said handle, wherein said locking mechanism comprises a member extending outward from a top side of the handle and a gasket in physical communication with the member and an interior of the conduit.

The aforementioned and other embodiments of the present application shall be described in greater depth in the drawings and detailed description provided below.

BRIEF DESCRIPTION OF THE DRAWINGS

These and other features and advantages of the inventions disclosed herein will be further appreciated, as they become better understood by reference to the detailed description when considered in connection with the accompanying drawings:

FIG. 8 progressively illustrates how a guide wire may be retrieved from lumen using the over tube;

DETAILED DESCRIPTION

The present application discloses an ergonomic handle that can be used to control the movement of the end of a catheter for positioning. The handle comprises a port that communicates with a lumen of the catheter. The handle further comprises a reservoir to hold saline or other fluid material, which can be used to provide lubrication of the guide wire as the guide wire traverses through it.

The present application is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present application is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
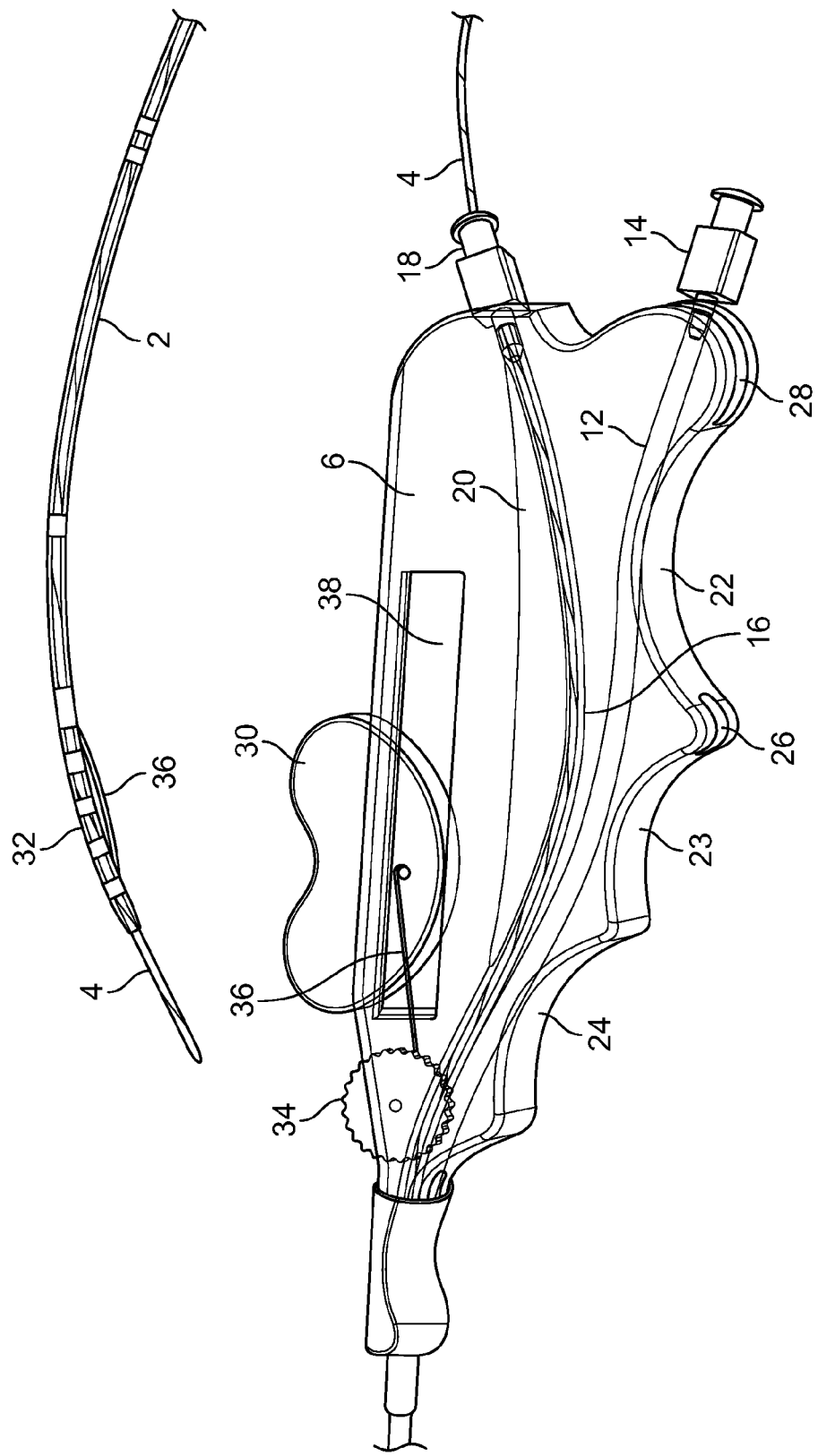
FIG. 1 depicts one embodiment of the catheter positioning handle.
Figure 2:
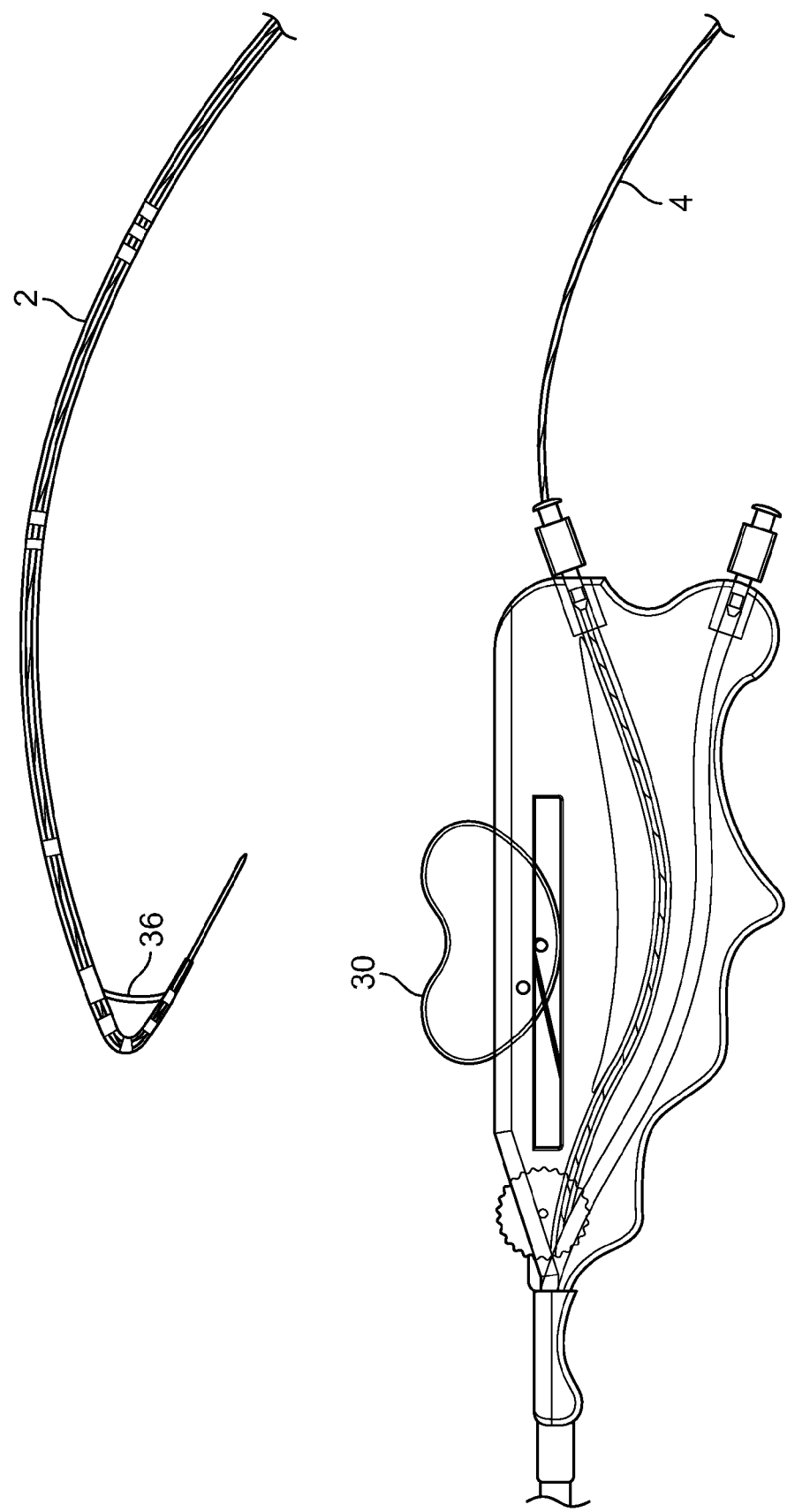
FIG. 2 depicts another view of one embodiment of the catheter positioning handle.
Figure 3:
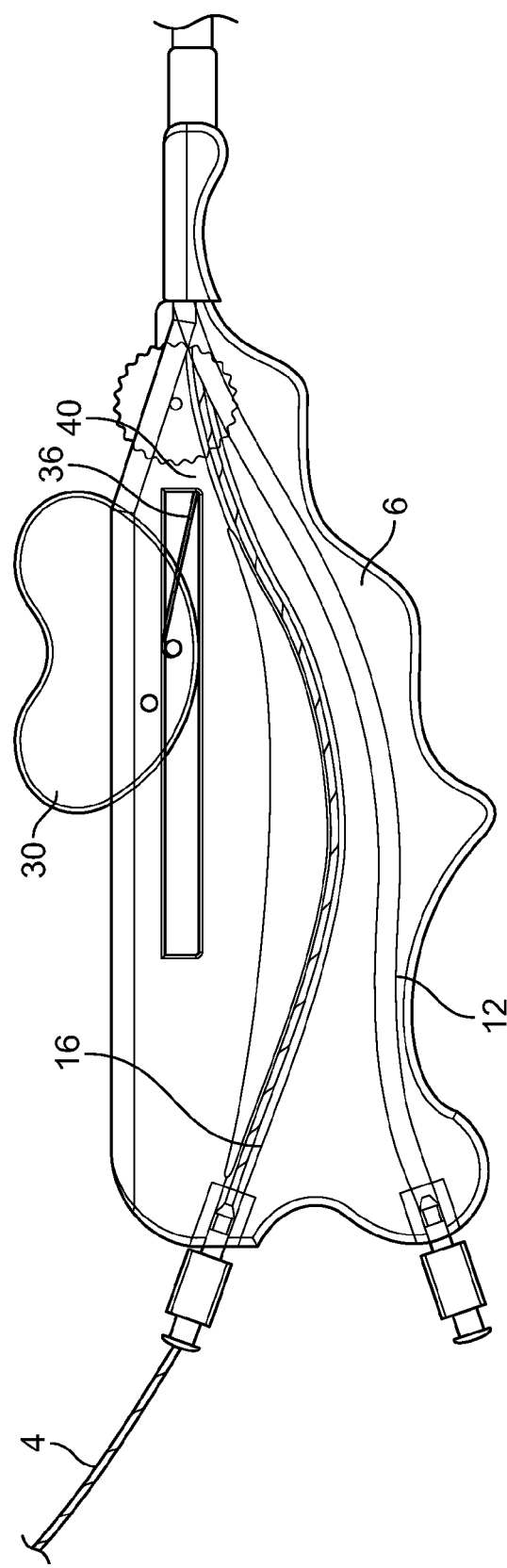
FIG. 3 depicts another view of one embodiment of the catheter positioning handle.
Figure 4:
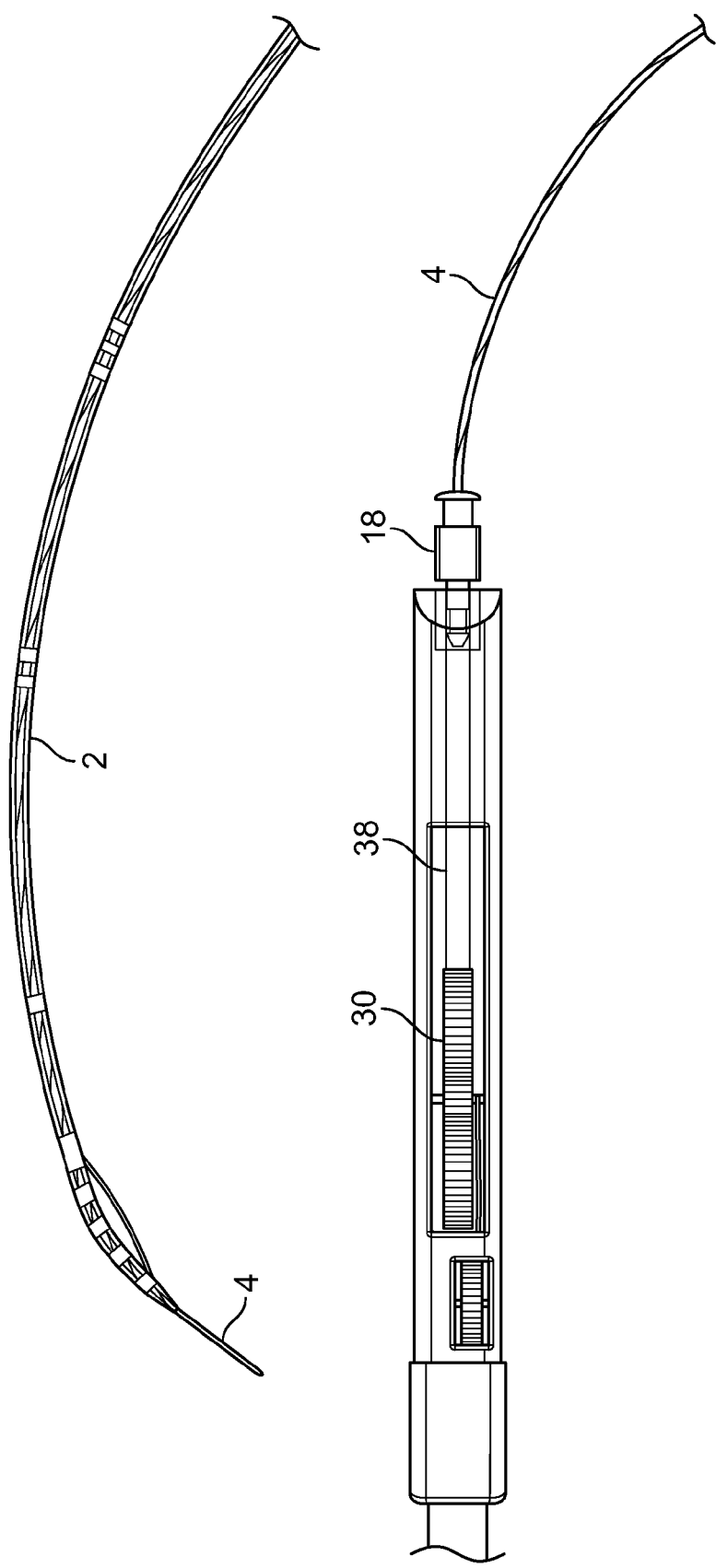
FIG. 4 illustrates a top view of the catheter positioning handle.
Figure 5:
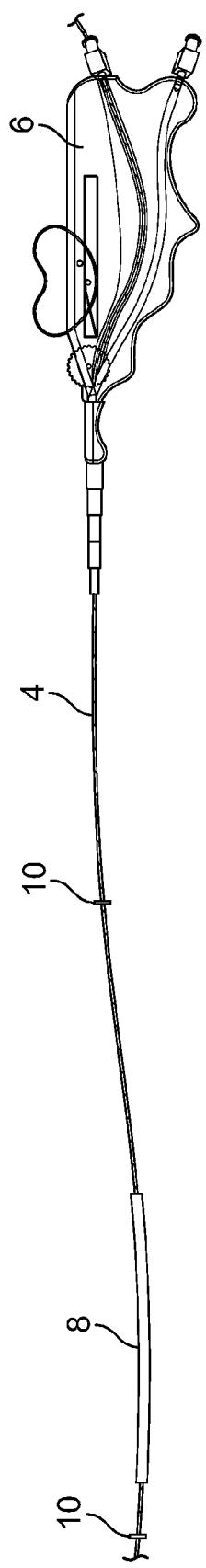
FIG. 5 depicts inclusion of an over tube structure relative to the catheter.
Figure 6:
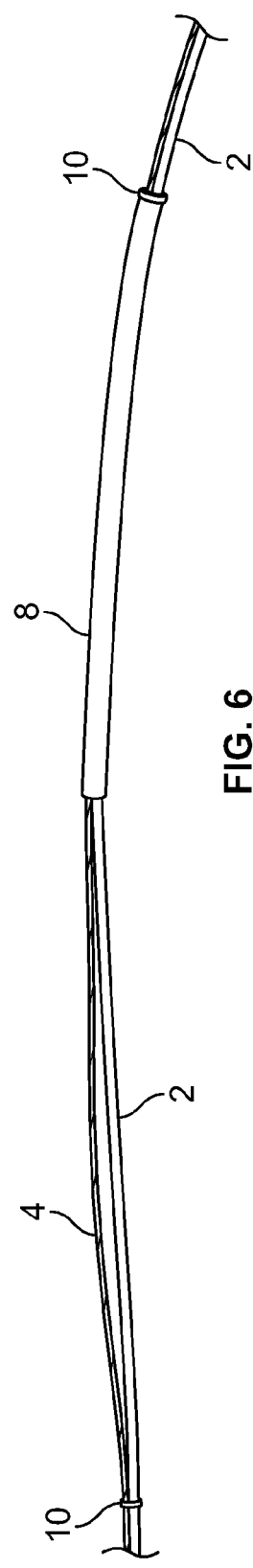
FIG. 6 illustrates how a guide wire may be retrieved from lumen using the over tube.
Figure 7:
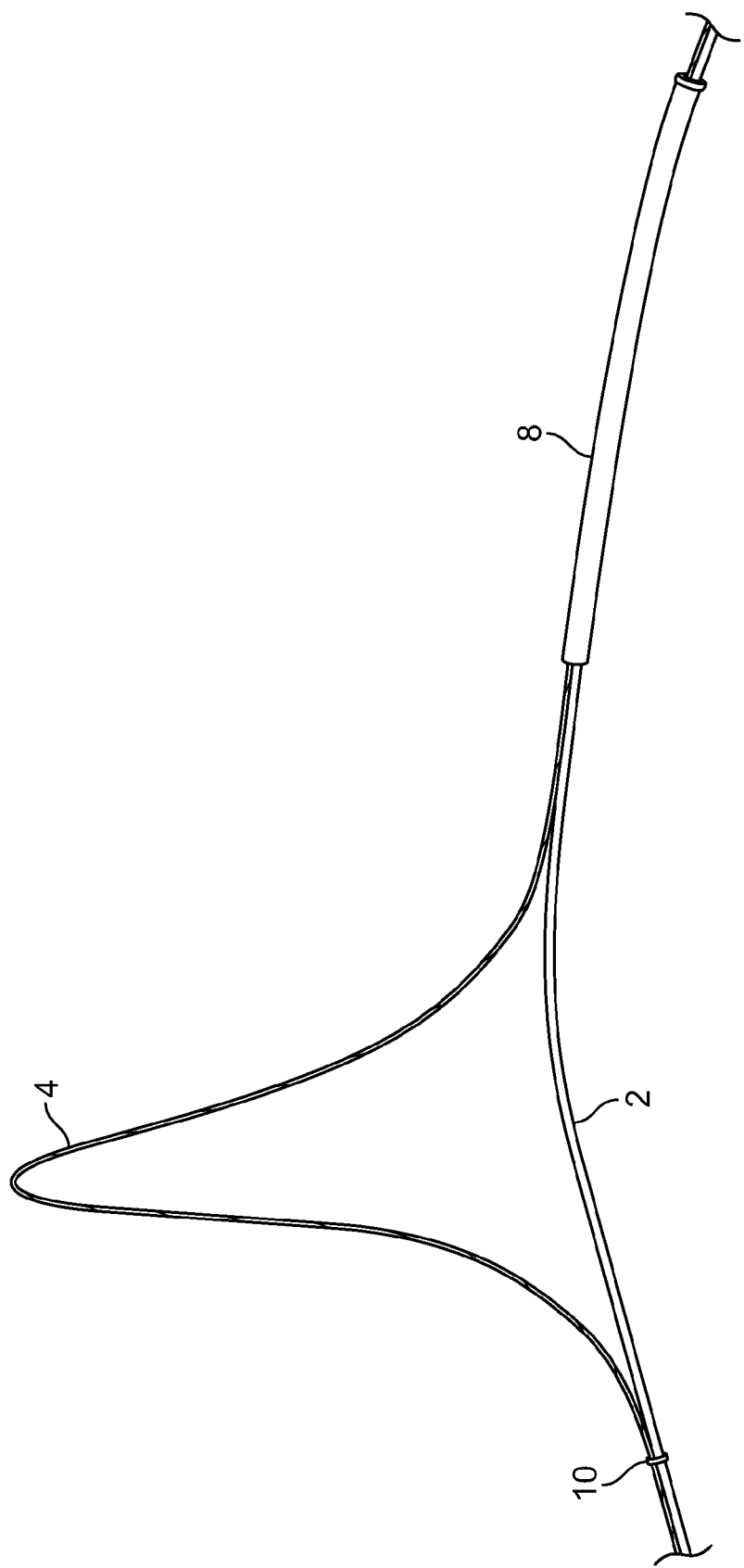
FIG. 7 illustrates how a guide wire may be retrieved from lumen using the over tube.

Referring to FIG. 1, in conjunction with FIGS. 2, 3 and 4, the handle 6 is formed to fit within the hand of a user. The handle 6 comprises a top surface that is substantially planar. The proximal end of the top surface curves down into a proximal side which extends down to the base of the handle. The base of the handle is formed with a plurality of peaks and valleys, in particular three valleys or grooves 22, 23, 24 with each side of the valleys or grooves 22, 23, 24 defined by a peak or elevated portion, such as 26, 28. The valleys are constructed and arranged to receive fingers of a user and, accordingly, may be differentially sized. Valley 22 may be sized to receive the small and ring fingers, valley 23 may be sized to receive the middle finger, and valley 24 may be sized to receive the index finger. However, actual placement of the fingers is at the option of the user. The distal end of the top surface tapers into a tip which physically meets or conjoins with the base of the handle.

In one embodiment, the handle has the following dimensions and associated ranges: The handle may be logically divided into a) a top region comprising a distance of 1.0 to 1.5 inches from the top surface downward into the handle, b) a middle region comprising a distance of 1.0 to 2.5 inches, more preferably, 1.5 to 2.5 inches from the top surface, and c) a bottom region comprising a distance of 2.0 to 5 inches, more preferably 2.5 to 5 inches from the top surface to the base of the handle.

In this manner, the handle is designed to have a shape that is ergonomically suitable for one-handed operation. That is, it may be palm held and used ambidextrously. As further described below, the pump reservoir, the wetting reservoir and the fine and gross motor movement and associated gearing enable one handed use. Further, the locking mechanism of the handle frees a nurse during important parts of any procedure and avoids cannulation losses that often occur because a nurse becomes distracted from watching the wire in order to care for the patient. The embodiments disclosed herein address such problems and enhance ease of use in catheterization procedures.

In one embodiment, the handle has a first conduit 12 which may be formed in the bottom region and extend from the proximal end of the handle to the tapered tip. One end of the first conduit opens to the proximal end of the handle, where a fitting 14 may be present. The fitting comprises an enclosure and central void or opening through which materials can pass into the conduit 12. The opposite end of the first conduit opens at the distal end of the handle, in particular the tapered tip, where it joins with a first lumen of the catheter 2. This conduit and lumen are used to transport materials, which may be liquid materials, through the lumen and into a body of a patient.

The handle has a second conduit 16 which may be formed in the middle region. One end of the second conduit opens to the proximal end of the handle, where a fitting 18 may be present. The fitting comprises an enclosure and central void or opening through which materials can pass into the conduit 16. The opposite end of the second conduit opens at the distal end of the handle 6, in particular the tapered tip, where it joins with a second lumen of the catheter 2. This conduit and lumen are used to transport a guide wire used for positioning the catheter into a body of a patient, such as into a duct or vessel.

One or more passages 20 may be provided in the handle. The guide wire passes through one passage. The second passage houses the drive wire of the catheter, and the third may be used for an injectable such as contrast. In one embodiment, as shown in FIG. 3, the handle may have three conduits 40, which may be formed in a lower portion thereof. One end of the third conduit 40, in one embodiment, communicates with a papillatome control. The opposite end of the third conduit opens at an opposite end of the handle, where it joins with a third lumen of the catheter 2 shown in FIG. 1. This conduit and lumen are used to transport a mechanism such as a papillatome used for positioning the guide wire and catheter into a body of a patient, such as into a duct or vessel. The drive wire of the catheter is advanced or retracted at the handle by the operator. This, in turn, causes the proximal end of the catheter to bow or flex as the drive wire is manipulated. The bowing or flexing allows the operator to align the catheter with the axis of the duct or vessel. When the axis of the catheter and the duct are in alignment, cannulation is accomplished and the guidewire can be advance through the catheter and into the duct.

Figure 8A:
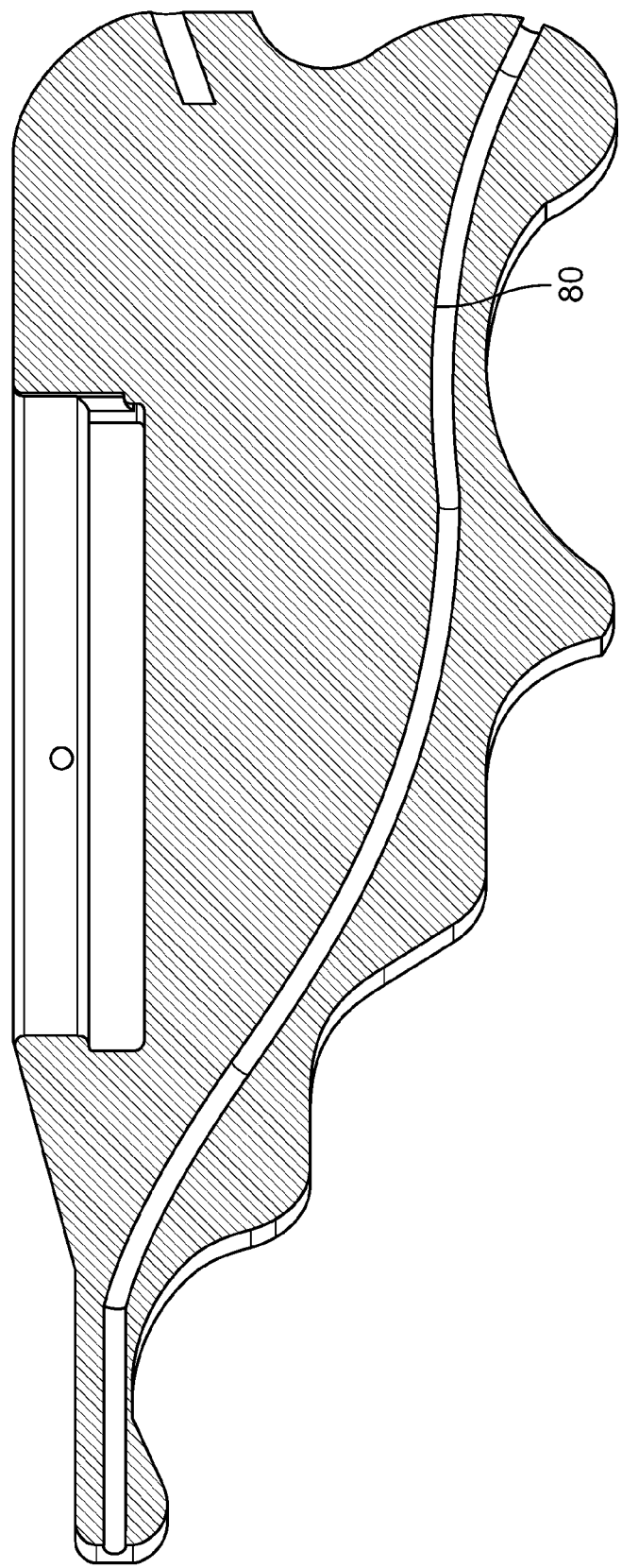
FIG. 8*a* illustrates a separate contrast lumen in one embodiment of the catheter positioning handle.

In one embodiment, the guide wire lumen, used for gross movement of the guide wire, and the contrast lumen are separated within the handle. The contrast lumen 80 is illustrated in FIG. 8a. In one embodiment, the contrast lumen is rigid to allow a syringe used to introduce contrast to be stably attached to the handle.

A common problem encountered during medical procedures is to keep long wires and catheters off the floor, so that they are not contaminated. Regardless of the procedure, it is preferable not to damage the catheter device because the device may be used again during that procedure. For example, another injection site may perhaps be located, or perhaps during a stone-removal procedure, the sphincterotomy that is created by the papillatome is not large enough as compared to the stone that is being removed. Because the devices used in endoscopy range in length from 180 cm to 420 cm, it is important to implement a system to protect the working end of the device. It is not unusual for this part to hit the floor or get tangled in bed sheets.

Figure 9:
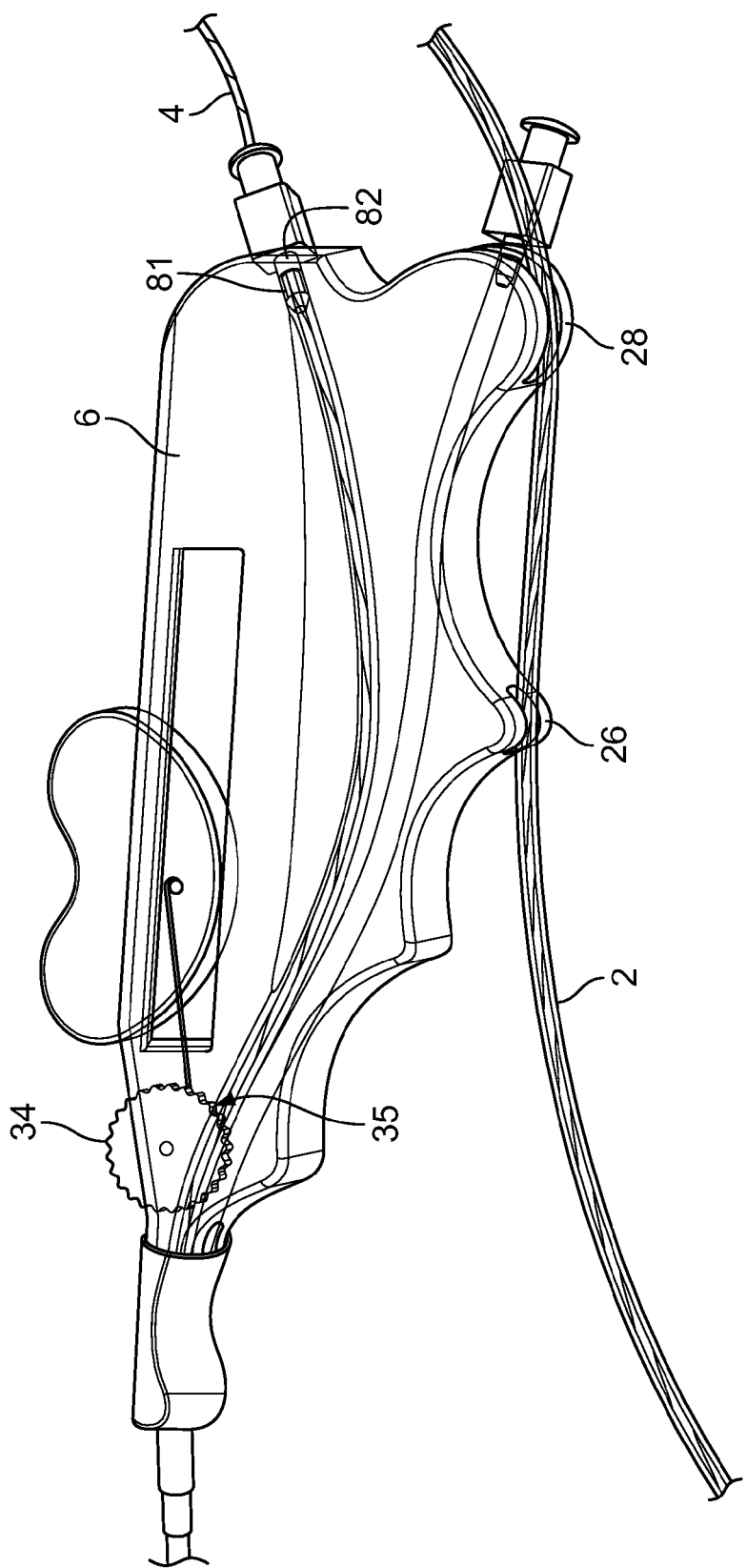
FIG. 9 illustrates an exemplary embodiment of a catheter catch integrated into the catheter positioning handle.

The inventions disclosed herein solve this problem by providing a catheter catch that protects the expensive end of the catheter by holding it in place. Referring to FIG. 9, the catheter catch is implemented by the slots within the peaks 26 and 28 that can be used for receiving the catheter when the device is not in use. The end of the catheter can then be wrapped around and connected to the handle base. This creates a loop and helps make sure the catheter doesn't fall on the floor. Furthermore, the catch reduces the length of the catheter by more than half and allows the catheter, when caught, to hang on a hook until needed later in the procedure. Due to the length of the catheter and guide wire, this feature aids in safety of the device, and reduces tangling of the catheter and guide wire, or tripping over the catheter and guide wire.

Referring back to FIG. 9, within the peaks 26 and 28 are slots, voids, or openings for receiving the catheter when the device is not in use. In particular the slots are formed by two protrusions preferably having a height that is greater than half the diameter of the catheter. For example, a 12 french catheter has a diameter of 0.158. The height of the protrusions is preferably greater than 0.079, or half of the diameter. In order to capture the catheter in the slot, the distance between the protrusions should be slightly less than the diameter of the catheter. Additionally, the slot may contain a flexible tacky material. This will allow for a range of catheter diameters. With such dimensions, and knowing the compression of the catheter material, the slot compression should be capable of securely receiving catheters having diameters in range of 7 to 12 french. It is essential for the catheter to fit snugly and securely within the slots so that, when a loose end of the catheter is fitted therein, it is capable of forming a loop that does not detach when hung or suspended in air.

In one embodiment, a papillatome control 30 may be provided on a top side of the handle. In the embodiment as shown, the control 30 is a slide that may be comfortably manipulated by the thumb while tightly gripping the handle with the fingers and palm of the hand. The control is slidably connected to the handle and travels within a slot 38 in the handle in this embodiment. Optionally, the control may have two peaks that define a valley there between, thereby enabling a user to rest a thumb in the valley and push on the peaks as needed to advance or retract the papillatome drive wire 36. The wire 36 is attached at top of handle which will bow or flex the papillatome at the proximal end of the catheter near the duct or vessel.

Manipulation of the end of the catheter is demonstrated by the relative positions of the control 30 and the distal end of the catheter shown in FIGS. 1 and 2. Sliding the control forward toward the catheter, positions the end of the catheter as shown in FIG. 1 by means of wire 36 that is connected to the control and the distal end of the catheter. Sliding the control back away from the catheter positions the end of the catheter as shown in FIG. 2. In one embodiment, the proximal end of the catheter may manipulated by 90 degrees or more to position the guide wire and the catheter. A thumb may be used to move the control 30 back and forth as required for fine movement of the wire as the handle is held in the same hand.

In one embodiment, a lock 34 (shown in FIG. 1) may be used to lock the guide wire in place. While locking the guide wire is important, it is also difficult as the wire is easily damaged when it is locked. In one embodiment, the lock may be an eccentric cam that, when rotated, pushes down on the lumen. The force of the cam on the lumen holds the guide wire in position. Inadvertent movement of the guide wire is thereby avoided.

In one embodiment, the lock is implemented as a rocking thumb wheel 34 and gasket 35 in physical communication with the wheel 34 and wire 4, as can be seen in FIG. 1. In one embodiment, the thumb wheel lock is not completely round but round with a bump. As long as the thumb wheel 34 is in the unlocked position, the wheel 34 does not touch the gasket 35. When it is locked, the bump puts a pressure on the gasket 35 and causes it to substantially flatten, thereby trapping the wire 4. Because the gasket or stopper comprises rubber, it will lock the wire by force of friction. In one embodiment, a rubber tube is placed around the wire 4, and under the lock thumb wheel 34, to protect the wire 4 and maintain fluid around the wire 4 (lubricity). Accordingly, a rubber surface functions to translate the locking pressure of the thumb wheel 34 while concurrently protecting the wire from breakage or fluid leakage.

Optionally, a larger rocking thumb wheel can be used on devices that require fine motor movements such as bowing for a papillatome. This will enhance the nurses' control in procedures such as cannulating the Sphincter of Oddi.

Figure 10:
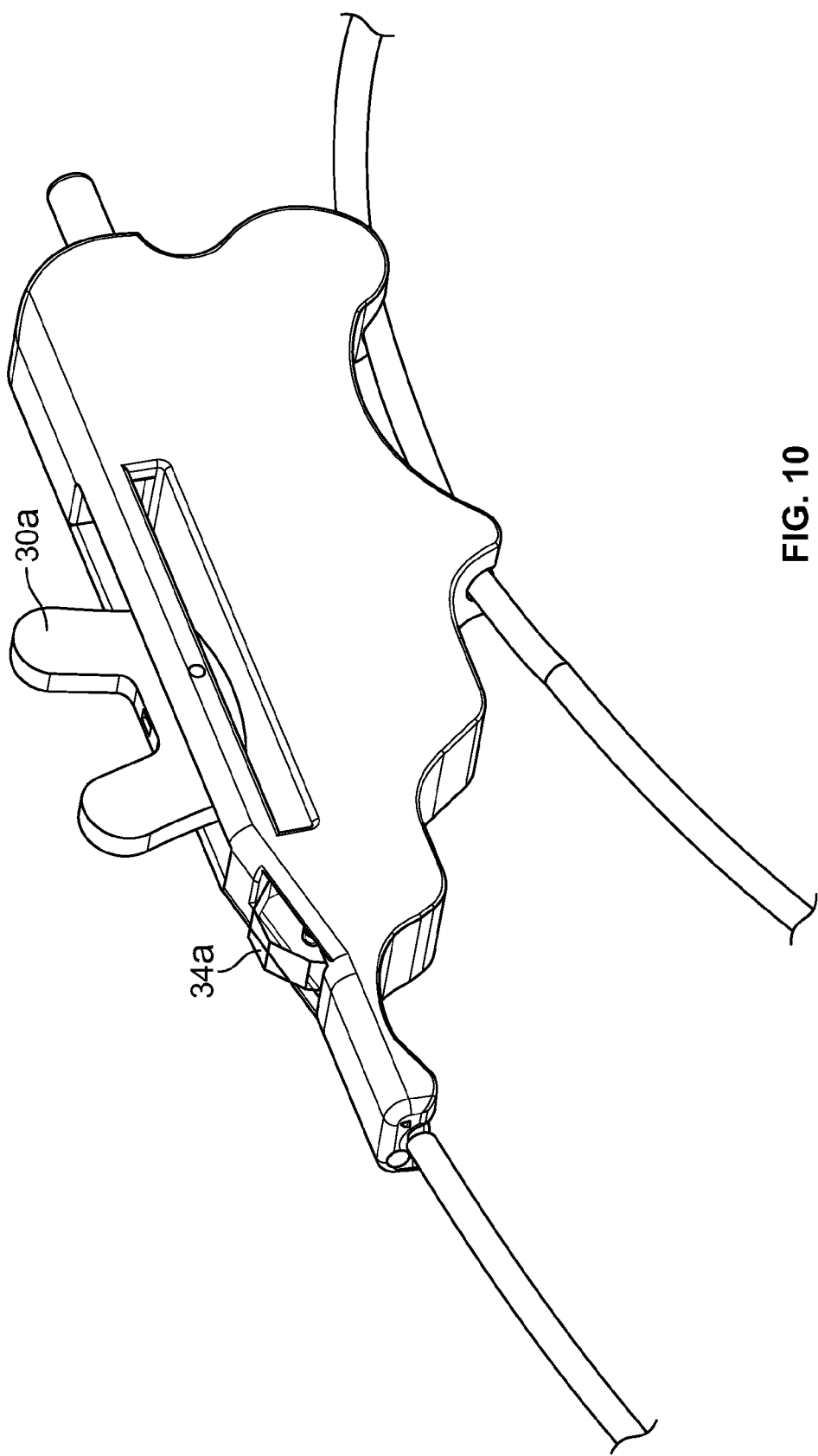
FIG. 10 depicts another embodiment of the handle incorporating a geared thumb wheel structure.

FIG. 10 illustrates another embodiment of the catheter positioning device. In certain medical procedures, it is required that the drive wire be advanced, or conversely that the catheter be pulled back on the wire. That is, the catheter and the drive wire must travel relative to each other. FIG. 10 shows an embodiment which makes use of a gearing mechanism to move the drive wire. Gearing is implemented in the thumb wheel 34a which translates a small movement by the user into a larger movement in the wire.

As an example of use, a basket used for biliary stone removal may be 3 cm wide by 6 cm long. To fully deploy the basket, the drive wire must travel 6 cm, which is a long distance to travel for a nurse operating the system with one hand. The thumb wheeled system disclosed herein is able to decrease the number of repetitive movements required to be made by the user by gearing down that travel, thereby requiring the user to move her thumb half the distance, as an example.

Figure 12:
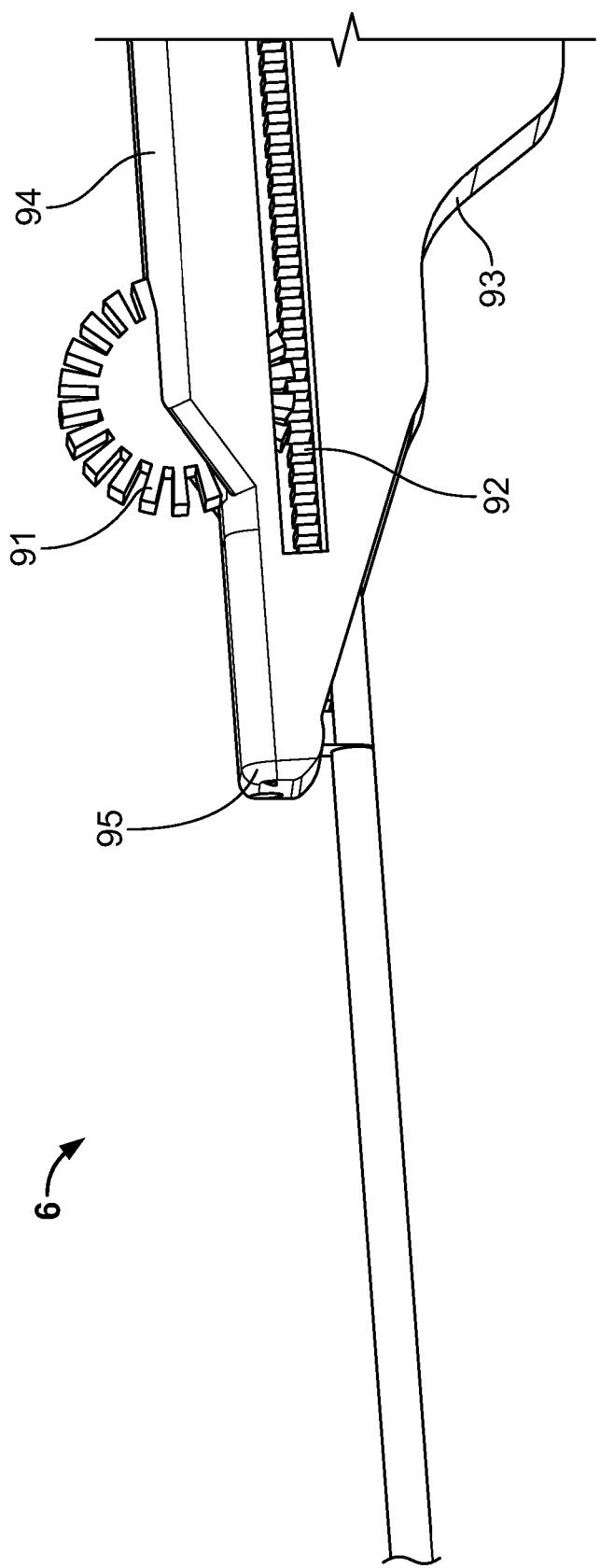
FIG. 12 illustrates an exemplary embodiment of a gearing system.

In one embodiment, the gearing mechanism is able to accomplish 6 cm of travel by the equivalent of 3 cm of user movement, as opposed to requiring 6 cm of user movement to accomplish 6 cm of travel. In these cases, a gear ratio of 2:1 would reduce this travel to three cm. Referring to FIG. 12, in one embodiment, this is accomplished by employing a rack 92 and pinion 91 gearing system. The handle 6 comprises a rotating gear structure 91 comprising a plurality of protrusions, divided by slots, which mate with a set of teeth on a linear member 92. A user preferably holds the handle 6 with a plurality of fingers extending around the bottom side 93 of the handle 6 and a thumb extending up and over the top side 94 of the handle. In operation, a user turns the rotating gear structure 91 a first distance with his thumb, causing the plurality of protrusions to apply pressure to the teeth which comprise the linear member 92 and thereby move the linear member 92 a second distance. The first distance is less than the second distance and, in one embodiment, is half the second distance. In one embodiment, a pinion of approximately ¾ inches in diameter can achieve a range of linear motion of 1.5 cm to 7 cm.

Accordingly, an operators thumb or hand can easily accomplish three cm of travel using the same amount of effort for moving six cm in a conventional system. In this instance, the catheter will be stationary and the drive wire will move. This allows the catheter to be connected to the handle for additional operations such as contrast injection or wire guide exchange. Additionally, in this embodiment, a fine toggle pivot may be provided for finer movements like those associated with moving a needle which requires movements in the range of 10 mm or less 30 a.

This gearing mechanism may also be deployed to manipulate the movement of other devices, such as snares, needles, cannulating catheters, balloon stone extractors, laser fibers, stone removal baskets, and stent deployment systems. Currently, operating snares greater than a length of 3 cm requires a substantial number of repetitive movements, using a conventional three ring handle, to cause the snare to travel long distances. By incorporating the aforementioned gearing mechanism into a conventional handle, one would minimize the number of repetitive movements. It should be appreciated that other gearing mechanisms could be employed, including two or more rotating structures where the final rotating structure interacts with an interior portion of the conduit to cause a wire to move or where the final rotating structure interacts with a linear member that then causes a wire in the interior of a conduit to move linearly.

Figure 11:
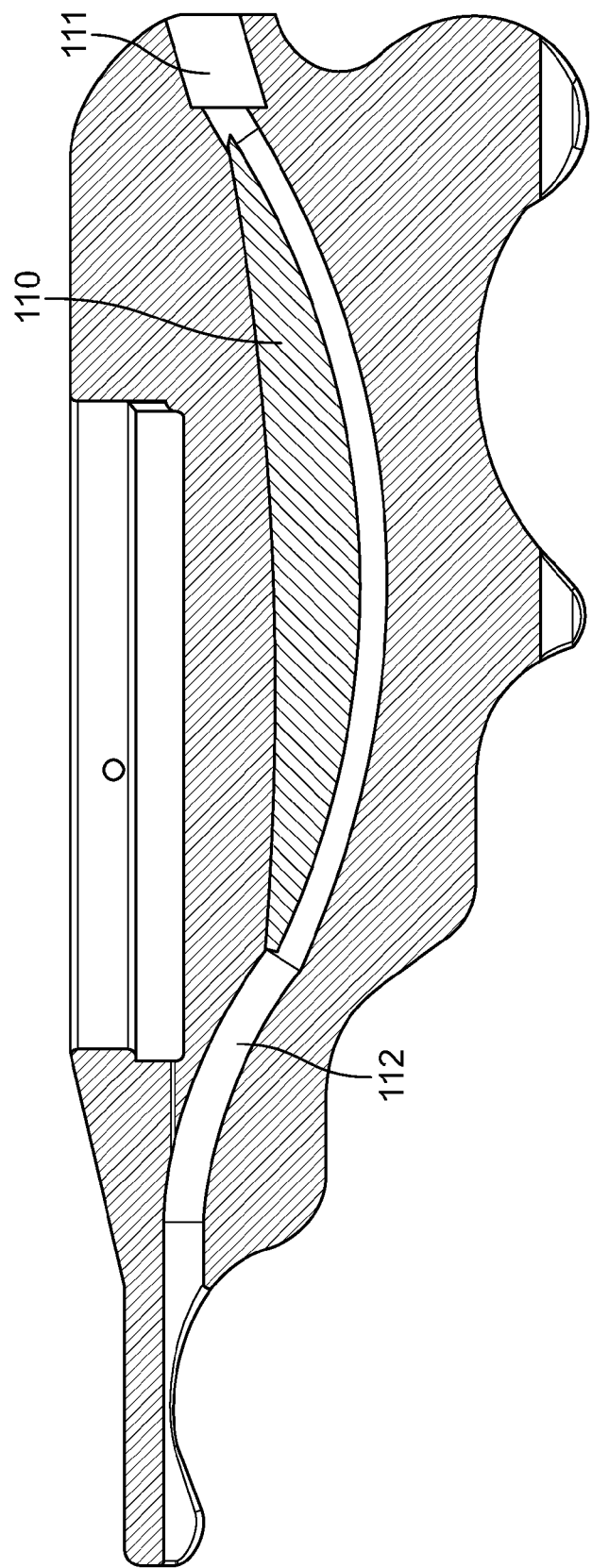
FIG. 11 illustrates one embodiment of a fluid reservoir in the catheter positioning handle.

In another embodiment shown in FIG. 11, the handle comprises a reservoir for wetting a wire guide. It should be appreciated that the reservoir is designed to contain any type of fluid, including water, air, contrast, any injectable fluid like Cyanoacrylate or Botox, or other therapeutic substances. Currently, wires used in certain medical procedures, such as GI and bronchoscopy procedures, stent placements, ERCP, pancreas cannulation, vascular vessel cannulation, peripheral vessel cannulation, urologic cannulation, minimally invasive spine, and orthopedic and laparoscopic work, are wetted by injecting water into the coil package housing the wire guide. The nurse then takes the wire out of the coil and feeds the slickened wire into the catheter. Advancing the wet wire is a slippery task, however. Often, the nurse does not realize that the wire is not advancing because the tactile feedback on a slick wire is misleading.

Here, in one embodiment, the wire is wetted after it is inserted into the catheter, by passing through a concave polygon shaped, in particular semi-circular shaped, fluid tank, well, or reservoir 110 (collectively "reservoir") that is contained within the handle and fully enclosed therein. By incorporating a wetting reservoir within the handle has several benefits, including reducing spilling or leaking of water from the wire guide coil package and enabling greater traction on the wire guide from the nurse's hand and improved tactile feedback.

The reservoir's semi-circular shape, namely a bulging base that extends downward and below a substantially planar top surface, creates a volume within which fluid collects at the bottom and below the points of fluid entry or exit, which are substantially in-line with the substantially planar top surface. The reservoir's concave shape therefore serves to keep the liquid in place since it is below the level of the filling lumen. Additionally, given the advancement of wire favors movement through the bulging base, the shape allows for the entire length of a wire to advance through the stored fluid, thereby continually filling the path in contact with the wire.

The reservoir 110 is fed by inlet and outlet tubes 111 and 112, respectively. Referring to FIG. 9, in one embodiment, the reservoir comprises a valve 81 on the side closest to the input port 82. The valve 81 is preferably a back flow valve which permits fluid to pass from the outside into the reservoir 110 but prevents fluid from flowing out of the reservoir 110. A fluid, such as water, is injected into the reservoir 110 using a suction or blowing mechanism, such as a pipette or water pistol. In one embodiment, the fitting 4, which is used to access the input port 82 and back flow valve 81, may be to the side of the handle.

As implemented within the handle, the reservoir 110 improves a health care provider's experience by not requiring the provider to wet the wire separately and having the water drip all over the floor and the nurse. The shape of the reservoir assures wire wetting, since the wire will always pass through water as long as any amount of water remains in the reservoir.

Figure 13A:
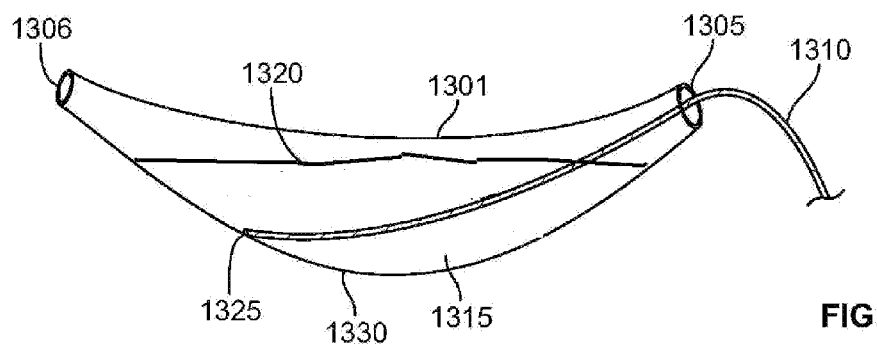
FIG. 13*a* illustrates a first embodiment of a wire passing into a fluid filled a reservoir.
Figure 13B:
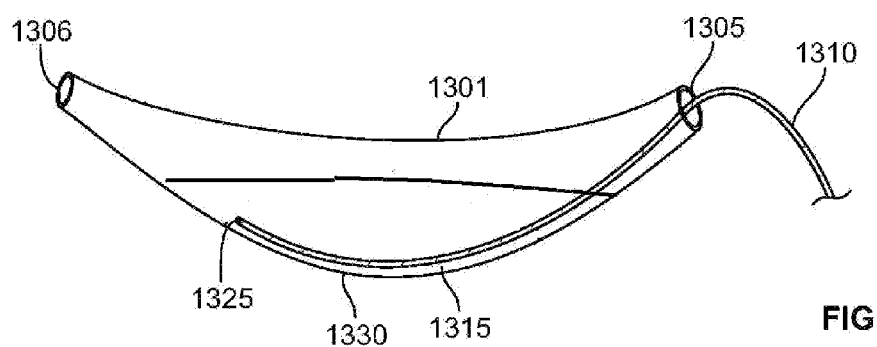
FIG. 13*b* illustrates a second embodiment of a wire passing into a fluid filled a reservoir.
Figure 13C:
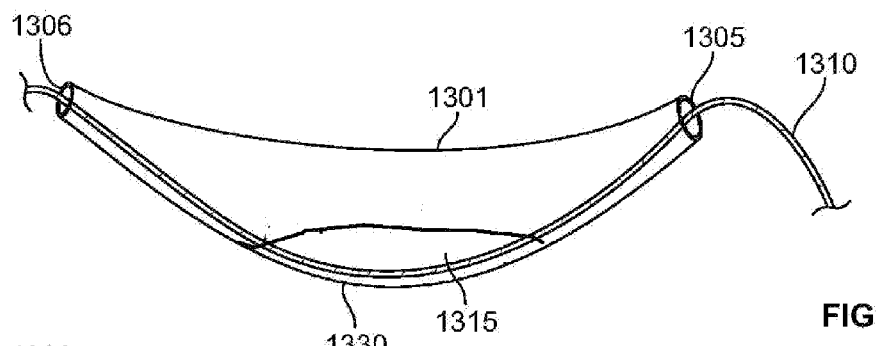
FIG. 13*c* illustrates a third embodiment of a wire passing into a fluid filled a reservoir.
Figure 13D:
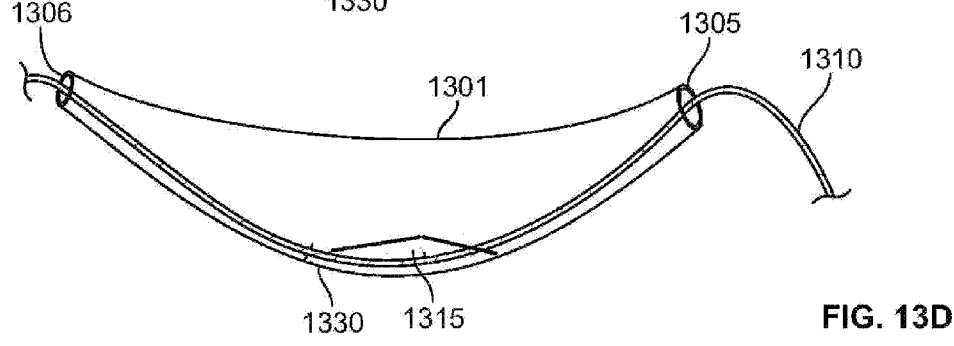
FIG. 13*d* illustrates a fourth embodiment of a wire passing into a fluid filled a reservoir.

Referring to FIGS. 13*a-d*, a reservoir 1301 within the handle has been filled with a liquid, such as water 1315, which fills to a level 1320 that is below entry point 1305, comprising a first gasket, and below exit point 1306, comprising a second gasket. In one embodiment, when the handle is held upright, the surface level 1320 of the water is below the first and second gaskets 1305, 1306. Referring to FIG. 13*a*, when a wire 1310 is passed into the reservoir, it engages the reservoir 1301 at a contact point 1325, typically near the reservoir's concave base 1330, due to the natural flexibility of the wire 1310 and force of gravity. As more tension is placed on the wire 1310, it travels along the reservoir's base, away from contact point 1325, and through gasket at exit point 1306, as shown in FIGS. 13*b* and 13*c*. The wire 1310 curves down and travels proximate to the reservoir's base 1330, which allows it to remain in contact with the fluid 1315, even when the fluid surface level decreases to a low level, as shown in FIG. 13*d*.

In another application of the reservoir, in cases where there is not a wire guide in use, such as injection therapy, the reservoir may be used for the storage of the injectable. In one embodiment, the handle comprises a rubber chamber and gasket, which, when compressed, will push fluid into the catheter and needle and, therefore, into tissue. This chamber may be filled in advance and may be used to express fluid by applying pressure to it. In one embodiment, a rocking wheel may be used to advance the needle and/or used to push the drive wire attached to the needle. The needle drive shaft is connected to the injection lumen and the outer catheter is the moving part. The catheter moves back on the needle drive shaft to expose the needle. In one embodiment, the system will be moved through the scope and with the help of an interface. Moving the outer catheter is important because manipulating the needle lumen may result in compression or kinking of the injection lumen.

In another application, the reservoir is filled with air and the handle is used in stone extraction procedures. The handle has a balloon mounted on the proximal catheter. One or several lumens run from the proximal end to the handle via the catheter. This catheter may contain lumens which infuse air to the balloon, infuse contrast above and below the balloon, via separate lumens, and/or manage a guidewire. Distally, the handle can provide a reservoir for wetting the wire, an air pump with gasket for inflating the balloon, and dual contrast lumens. To inflate the balloon, a gasket incorporated into the reservoir could be used to force air through the reservoir, through the catheter, and into the balloon. It should be appreciated that any pumping action could be used to force air through the reservoir and into the balloon catheter, including the pipette or pistol.

As discussed above, in one embodiment, the catheter 2 has multiple lumens and the guide wire 4 traverses one of the lumens. The guide wire enters one end of the handle 6 and exits an opposite end of the handle and into the catheter. The guide wire traverses the handle and the catheter, and is of sufficient length to materially extend beyond the catheter and the handle at both ends thereof. In one embodiment, a special catheter is preferably used in conjunction with the handle embodiments disclosed herein. More specifically, the lumen of the catheter 2 that houses the wire has an opening that permits access to the guide wire at a portion of the wire that is remote from the end of the catheter where the wire is inserted into the lumen.

Referring to FIGS. 5, 6, 7 and 8, in one embodiment, the lumen may have an annular cross section, with a longitudinal slit, opening, void, or cut (collectively, slit) that forms an access point in the lumen through which the guide wire traverses. The slit provides access to the wire at a portion of the lumen that is remote from the end of the catheter, and between the handle and the opposite or proximal end of the catheter. The guide wire 4 can be removed from the lumen of the catheter 2, as progressively shown in FIG. 6, FIG. 7, and FIG. 8, and then advanced and retracted at this point of the catheter 2 by grasping and pushing or pulling the guide wire. In one embodiment, the catheter may comprise a thin wall, with the guide wire forced out of the thin wall for access, if and when desired.

In an alternative embodiment, the lumen may be slightly less than annular, while still retaining the wire, such as by having a "C" shape, so that part of the lumen is open. The opening is sufficiently small in its normal and under-formed dimension to retain the wire, but may be deformed and enlarged to allow a portion of the wire to be pulled out and manipulated, such as by the physician.

In one embodiment, an over tube 8 (shown in FIGS. 5, 6, 7 and 8) is slide-ably fitted over the catheter 2. The over tube is a sliding sheath that may slide to a first position, which reveals the slit through which the guide protrudes, and also slide to a second position, which covers the slit. In one embodiment, the over tube comprises an annular cross section and has a sufficient length to cover the slit in the lumen of the catheter. Stops 10 may be affixed to the catheter to limit the travel of the over tube along the catheter. This unique wire handling system with the slidable sheath or window provides a physician access to the wire when fine cannulation is required, such as with biliary work, including GI and bronchoscopy procedures, stent placements, ERCP, pancreas cannulation, vascular vessel cannulation, peripheral vessel cannulation, urologic cannulation, minimally invasive spine, and orthopedic and laparoscopic work. Guide wires allow removal of such access when it is not necessary. This apparatus is advantageous because the catheter does not split or peel away when the wire is pulled out. Instead the catheter is already split and is slide-ably exposed using the over tube to allow for wire access.

Referring back to FIG. 1, in use, and by way of example, an assistant, such as a nurse, handles the guide wire 4 and the multi-lumen catheter 2 and initiates advancement of the guide wire through the handle 6 and the catheter. The assistant may advance the guide wire from a position that is to the rear of the handle and fitting 18. The physician may choose to access the guide wire during the procedure for fine movement and manipulation into, for example, a duct. The physician may position the multi-lumen catheter in the duct and push the guide wire through the catheter into the duct. Contrast material may be injected through fitting 14 and into the multi-lumen catheter to ascertain that the correct duct or position has been achieved prior to advancing the guide wire.

Alternatively, the guide wire may be pushed out of the end of the catheter, with the guide wire used as a probing instrument to find a duct opening. Access to the guide wire may be gained through the slit or opening by providing a compression force on the lumen forward of the opening, such by lock 34. The wire is retrieved from lumen through the slit, as explained with reference to FIGS. 6, 7 and 8. The physician may grasp the wire and use the papillatome control 30 to manipulate it to position the end of the wire in the duct.

After manipulation, the over tube 8 (shown in FIGS. 5, 6, 7 and 8) is positioned over the slit to cover the opening. Injection of contrast and advancement of the guide wire may now take place from the assistant's position. If the physician subsequently desires to take control of the guide wire, the over tube slides away from the slit, and the guide wire is lifted from the lumen through the opening. With this over tube covering the opening in the lumen, the guide wire is stabilized and supported axially, so that the assistant can advance the wire from the distal end of the catheter.

The device and method are useful with an ERCP scope channel area, which is near where the physician's hands are positioned. The assistant operates at the distal end of the catheter, which is approximately 100 cm from the physician. The handle allows the assistant to handle the guide wire and inject contrast in a controlled situation. The lock allows the wire to be locked in place. A sheath or protective layer may be positioned between the lock and the catheter to protect the catheter. The mechanism such as the papillatome may be manipulated without using a second hand. The second hand, instead, may be used to inject contrast, or work with the patient.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

What is claimed is:

1. A catheter control device for use in medical procedures, the catheter control device comprising a handle having a top side, bottom side, left side, and right side, the handle comprising an enclosure having a first space and a second space, wherein said first space and said second space are not in fluid communication with each other, wherein said first space extends through the enclosure from the left side to the right side, and wherein the second space comprises a liquid reservoir constructed and arranged to receive and hold a liquid, and the liquid reservoir comprises an arcuate and concave base that extends into a bottom region of the handle, and
wherein the catheter control device further comprises a movable wire, and wherein a portion of the movable wire is present in the liquid reservoir near the arcuate and concave base of the second space.

2. The catheter control device of claim 1, wherein the bottom side and top side converge into a tapered point on the left side.

3. The catheter control device of claim 2, wherein the first space is a conduit, and wherein said conduit extends through said tapered point on the left side.

4. The catheter control device of claim 1, wherein the bottom side has a surface that comprises a peak and wherein said peak is divided to form a slot in the peak, and wherein the slot is constructed and arranged to receive and hold a catheter in the slot.

5. The catheter control device of claim 1, further comprising a fitting extending from said right side and communicating with an input port for the liquid reservoir, wherein the movable wire passes through the fitting, and the fitting is constructed and arranged to position the movable wire in the liquid reservoir adjacent to the arcuate and concave base of the liquid reservoir.

6. The catheter control device of claim 5, further comprising a back flow valve positioned within the conduit and proximate said input port.

7. The catheter control device of claim 1, further comprising a locking mechanism configured to lock a wire within said first conduit, wherein said locking mechanism comprises a member extending outward from the top side and a gasket in physical communication with the member and an interior of the first conduit.

8. The catheter control device of claim 1, further comprising a papillatome control, wherein said papillatome control extends outward from top side of the handle and is slidably connected to the handle.

9. A catheter for use in the catheter control device of claim 1, wherein said catheter comprises a sheath having an opening therein and a cylindrical member configured to slide from a first position to a second position over said sheath.

10. The catheter of claim 9, wherein the first position covers said opening and wherein the second position does not cover said opening.

11. The catheter control device of claim 1, wherein the liquid reservoir of the second space has an increasing interior volume from the input port to the center of the liquid reservoir.

12. The catheter control device of claim 1, wherein the right side comprises a first port for the liquid reservoir and the left side comprises a second port for the liquid reservoir, and wherein the liquid reservoir of the second space has an increasing interior volume from the first port to the center of the liquid reservoir and wherein the liquid reservoir of the second space has an increasing interior volume from the second port to the center of the liquid reservoir.

13. The catheter control device of claim 1, wherein the right side comprises a first port for the liquid reservoir and the left side comprises a second port for the liquid reservoir, and wherein a top of the liquid reservoir is below the first port and the second port.

14. The catheter control device of claim 1, wherein the right side comprises a fitting that communicates with an input port for the liquid reservoir and the left side comprises an exit point for the liquid reservoir, and wherein the liquid reservoir is sealed to hold a liquid in the liquid reservoir.

15. The catheter control device of claim 1, wherein an input port for the liquid reservoir and an exit point for the liquid reservoir are positioned above a center of a top of the liquid reservoir.

16. The catheter control device of claim 1, wherein the liquid reservoir has an arcuate top portion, and an input port for the liquid reservoir and an exit point port for the liquid reservoir are positioned above a center of the top portion of the liquid reservoir.

17. A handle for use in biliary work, gastrointestinal procedures, bronchoscopy procedures, stent placements, ERCP, pancreas cannulation, vascular vessel cannulation, peripheral vessel cannulation, urologic cannulation, minimally invasive spine, orthopedic procedures, or and laparoscopic procedures, wherein said handle has a top region, middle region and bottom region and wherein said handle comprises:

an enclosure;

a liquid reservoir formed within said enclosure, wherein said reservoir is located substantially within the middle to bottom region of the handle and wherein said liquid reservoir is constructed and arranged to receive and hold a liquid, and the liquid reservoir comprises an arcuate and concave base that extends into a bottom region of the handle;

an input port on a first side of the handle and proximate to the top surface of the liquid reservoir; and a fitting extending outwardly from said right side in fluid communication with the input port.

18. The handle of claim 17 wherein the handle comprises a bottom side and a top side and wherein the bottom side and top side converge into a tapered point on a second side of the handle.

19. The handle of claim 18 wherein the handle further comprises a conduit extending from a first side of the handle through said tapered point on the second side.

20. The handle of claim 17, wherein the handle comprises a bottom side, wherein the bottom side has a surface that comprises a peak, and wherein the peak is divided to form a slot in the peak, and wherein the slot is constructed and arranged to receive and hold a catheter in the slot.

21. The handle of claim 17 further comprising a locking mechanism configured to lock a wire within a conduit located in said handle, wherein said locking mechanism comprises a member extending outward from a top side of the handle and a gasket in physical communication with the member and an interior of the conduit.

22. The handle of claim 17, wherein the fitting extending outwardly from said right side is constructed and arranged to position a movable wire into the liquid reservoir adjacent to the arcuate and concave base of the liquid reservoir.

23. The handle of claim 17, wherein the liquid reservoir of the second space has an increasing interior volume from the input port to the center of the liquid reservoir.

24. The handle of claim 17, wherein the input port on the first side of the handle is above a top surface of the liquid reservoir.

25. The handle of claim 17, wherein the liquid reservoir is sealed to hold a liquid in the liquid reservoir.

26. The handle of claim 17, wherein an input port for the liquid reservoir and an exit point for the liquid reservoir are positioned above a center of a top of the liquid reservoir.

27. The handle of claim 17, wherein the liquid reservoir has an arcuate top portion, and an input port for the liquid reservoir is positioned above a center of the top portion of the liquid reservoir.

28. The handle of claim 17 wherein the fitting extending outwardly from said right side is constructed and arranged to position a movable wire into the liquid reservoir adjacent to the arcuate and concave base of the liquid reservoir.

* * * * *